(12) United States Patent
Hong (10) Patent No.: US 10,737,288 B2
(45) Date of Patent: Aug. 11, 2020

(54) AUTOMATIC SPIN COATING SYSTEM

(71) Applicant: Bin Hong, Rockville, MD (US)

(72) Inventor: Bin Hong, Rockville, MD (US)

( * ) Notice: Subject to any disclaimer, the term of this patent is extended or adjusted under 35 U.S.C. 154(b) by 144 days.

(21) Appl. No.: 15/902,867

(22) Filed: Feb. 22, 2018

(65) Prior Publication Data

US 2019/0255556 A1 Aug. 22, 2019

(51) Int. Cl.
| | | |
|---|---|---|
| *G01N 1/00* | (2006.01) | |
| *B05C 11/08* | (2006.01) | |
| *G01N 1/28* | (2006.01) | |
| *G01N 33/80* | (2006.01) | |

(52) U.S. Cl.
CPC ............ *B05C 11/08* (2013.01); *G01N 1/2813* (2013.01); *G01N 33/80* (2013.01)

(58) Field of Classification Search
CPC ....................................................... G01N 1/00
See application file for complete search history.

(56) References Cited

U.S. PATENT DOCUMENTS

2007/0207485 A1* 9/2007 Deppermann ........... G01N 1/04
435/6.12

* cited by examiner

*Primary Examiner* — Jyoti Nagpaul
(74) *Attorney, Agent, or Firm* — Trojan Law Offices (57) ABSTRACT

An automatic spin coating system includes a dispensing assembly and a base assembly. The dispensing assembly comprises a dispensing device that contains a coating material, a pulley assembly, a drive gear, and a smooth wheel. The base assembly includes a coating plate for receiving the coating material, a chuck plate for securing the coating plate, a stepper pin capable of engaging the drive gear of the dispensing assembly, and an electric motor for spinning the chuck plate. The dispensing device further comprises a vessel assembly to provide immobilization of the dispensing device, and a tubing assembly to control the flow of the coating material. The dispensing device is connected to the pulley assembly, which in turn is connected to the drive gear and the smooth wheel. When the chuck plate spins, the stepper pin revolves and touches the drive gear so as to rotate the pulley assembly, and meanwhile, the coating material is dispensed and coated on the coating plate in different circles without overlap between circles. In one embodiment, the stepper pin has a gear with different sizes of teeth that allow different degrees of movements of the dispensing device. The coating material is then dispensed from a first circle to a second circle.

5 Claims, 13 Drawing Sheets

AUTOMATIC SPIN COATING SYSTEM

FIELD OF THE INVENTION

The present invention relates to a spin coating device, and in particular, a device for automatically developing blood films.

DESCRIPTION OF RELATED ART

Analysis of blood film is an important laboratory test for clinical examination and diagnosis of various diseases. Blood smear is one type of blood film and has been widely used to examine the health and relative counts of blood cells. Blood smear is often prescribed to identify immature, abnormal, or diseased blood cells, and also monitor patients' undergoing treatments. Many diseases and disorders (including but not limited to cancers, anemia, bone marrow disorders, malaria, lymphoproliferative disease, liver failure, renal diseases, sepsis and etc.) can affect the status of blood cells in terms of their number, function, and lifespan. Additionally, symptoms of fatigue, unexpected or severe infection, bone pain, unexplained jaundice, sudden weight loss, skin rash and etc. can be diagnosed by blood smear.

Blood smears are typically prepared by placing a drop of blood over a microscope slide, and then a spreader slide is used to disperse the blood over the microscope slide. This technique develops the monolayered blood film with feathered edge for where blood cells are spread apart so that they can be differentiated and examined individually. With manual techniques, preparation of the blood smear can easily fail, causing irregular spread of blood with waves, holes, ridges, jagged tail, and damaged cells. Common causes of poor manual blood smear include the size of the blood drop being too large or too small, failure to keep constant contact between slides, failure to keep right angle between slides, failure to use uniform force across slides, and so on. Therefore, manual blood smear requires technical training and clinical experience and hardly prevents human errors during preparation.

Automated blood smearing can minimize human errors and be achieved by traditional spin coating, where at high spin speed (1,000-5,000 revolutions per minute; RPM), the coating material spreads over the substrate, spins off the edge, and forms a thin film on surface. Volatile organic solvent is typically used to dissolve the coating materials for low surface tension and high evaporation rate. The coating process is highly dynamic and out-of-equilibrium, causing topographic result of coated film not finely tunable. Coating defects like bubbles, comets, streaks, flares, swirl pattern, incomplete coating and pinholes are frequently observed. The powerful centrifugal force can also alter the morphology and affect the integrity of the coating materials. In addition, spin-off of excess coating materials from surface in the form of aerosol can be hazardous.

The object of the present invention is to improve traditional spin coating technology by overcoming its intrinsic defects and resolving its operational variations. This invention provides coating of uniform films with high reproducibility, preserves the intactness of coating materials, eliminates human errors, external contamination, and spin-off of excess coating materials, and facilitates computer aided target recognition and data interpretation. The present invention overcomes the aforementioned problems by employing an automatic spin coating system having a low spinning speed, a dispensing system mimicking the spreader slide, a translational mechanical system combining both angular and linear movements, and active bio-friendly temperature control for preservation of coating materials. Specifically, the design of the nozzle of the present invention will not only prevent common contaminations that often occur in manual blood smears, but also preserve the blood sample by only delivering the exact amount needed for the automatic coating process.

SUMMARY OF THE INVENTION

The present invention is a spin coating system that automatically dispenses a coating material on a coating plate. The spin coating system comprises a dispensing assembly and a base assembly. The dispensing assembly includes a dispensing device having a vessel (such as a tube) containing the coating material to be dispensed and a tubing assembly to deliver the coating material and control the flow. The dispensing device is connected to a pulley assembly, which in turn is connected to a drive gear and a smooth wheel. Before the drive gear is actuated, the dispensing device dispenses the coating material in a circle. When the drive gear is actuated, it drives the pulley assembly so as to move the dispensing device from a first position to a second position. In this way, the dispensing device can be moved to dispense the coating material in different circles.

The base assembly, located below the dispensing assembly, has a coating plate for receiving the coating material dispensed by the dispensing assembly. The coating plate is secured in a chuck plate that is capable of spinning and rotated by a motor. The chuck plate has a stepper pin located in a position to engage the drive gear of the dispensing assembly. When the chuck plate spins, the stepper pin revolves around the spin axis. As the stepper pin makes a complete revolution, it engages the drive gear of the dispensing assembly. This causes the pulley assembly to move the dispensing device such that the coating material is dispensed in different circles on the spinning coating plate.

The dispensing of the coating material at different circles on the coating plate can be controlled by a gear head on the stepper pin. In a preferred embodiment of the invention, the gear head on the stepper pin has different sizes, such that each size translates into a different degree of movement of the dispensing device when the stepper pin makes contact with the drive gear.

In one embodiment of the automatic spin coating system, there is provided a spin coating method. The chuck plate rotates by a motor. The dispensing devices moves from the first position to the second position by the pulley assembly, while discharging the coating material from the dispensing device toward the coating plate in different circles. The dispensing device moves when the drive gear is rotated by the stepper pin, which causes the different movement of the dispensing device. The coating plate spins with the chuck plate such that the coating material is dispensed on different circles of the coating plate.

These and other objects, advantages, and features of the invention will be more fully understood and appreciated by reference to the detailed description of the current embodiments and the drawings.

BRIEF DESCRIPTION OF THE DRAWINGS

FIG. 2F also illustrates a perspective view of the drive gear of the dispensing assembly.

DETAILED DESCRIPTION OF EMBODIMENTS

I. Overview

Figure 1A:
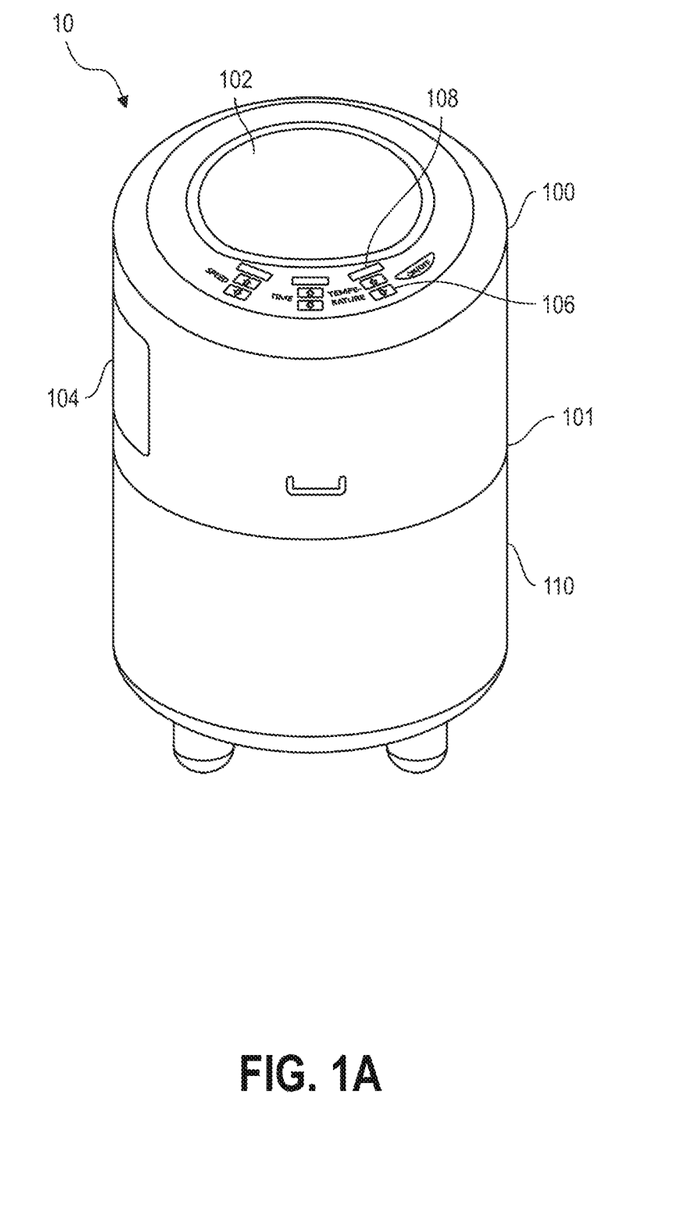
FIG. 1A illustrates a perspective view of an automatic spin coating system having a top housing and a bottom housing.
Figure 1B:
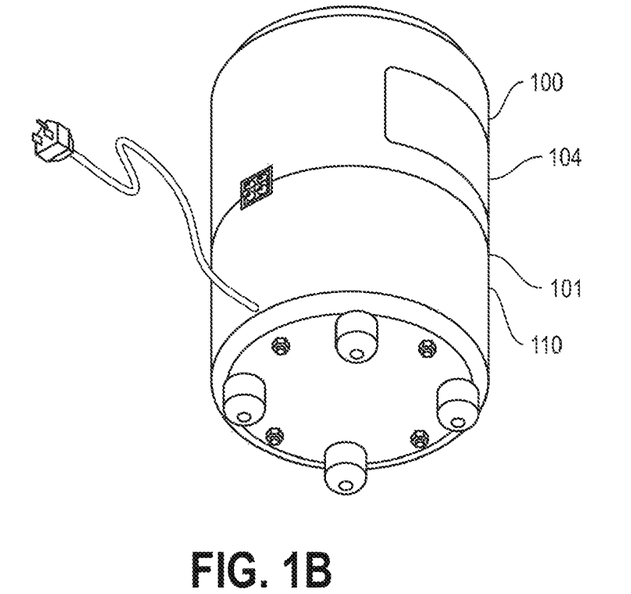
FIG. 1B illustrates a bottom perspective view of the automatic spin coating system.
Figure 2A:
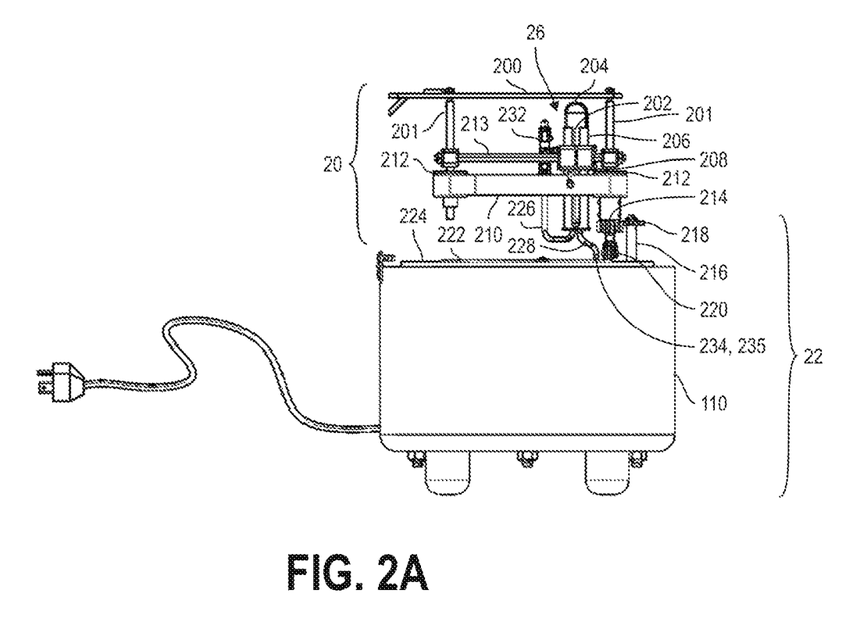
FIG. 2A illustrates a side view of the dispensing assembly and a bottom housing of the automatic spin coating system shown in FIG. 1A, where the dispensing assembly includes a dispensing device, a pulley assembly, a drive gear, and a smooth wheel.

An automatic spin coating system, shown in FIGS. 1A and 1B, is comprised of a top housing 100 and a bottom housing 110. FIG. 2A illustrates a dispensing assembly 20 inside of the top housing 100. The dispensing assembly 20 is capable of dispensing a coating material 202 to a coating plate 222 located in the bottom housing 110.

The automatic spin coating system 10 can be used for coating a variety of coating materials 202, including but not limited to biospecimens (including human specimens and body fluids, such as whole blood, blood plasma, blood serum, saliva, urine, bone marrow, cerebrospinal fluid, pericardial fluid, pleural fluid, umbilical cord blood, milk, and etc., whether raw or diluted, original or derived products for clinical research, examination, detection and diagnosis; and cell cultures, culture media, biologic production media, lysate, eluate, extraction, fermentation media, brewing media, and etc. for laboratory examination of activity, viability, secretion, excretion, expression, and morphology involving, relating to, or derived from living organisms) and biological and non-biological, organic, inorganic and polymeric, fluids, solutions, dilutions, sols, gels, emulsions, solvents, mixtures, suspensions, colloids, and etc.

II. Structure

Figure 1C:
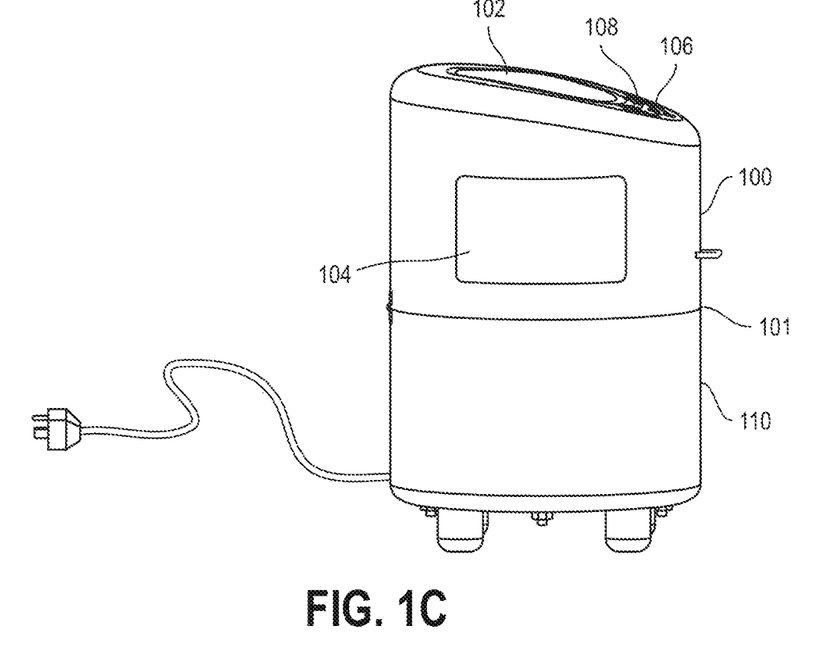
FIG. 1C illustrates a side view of the automatic spin coating system shown in FIG. 1A, having a transparent window for inspection of a coating process.
Figure 1D:
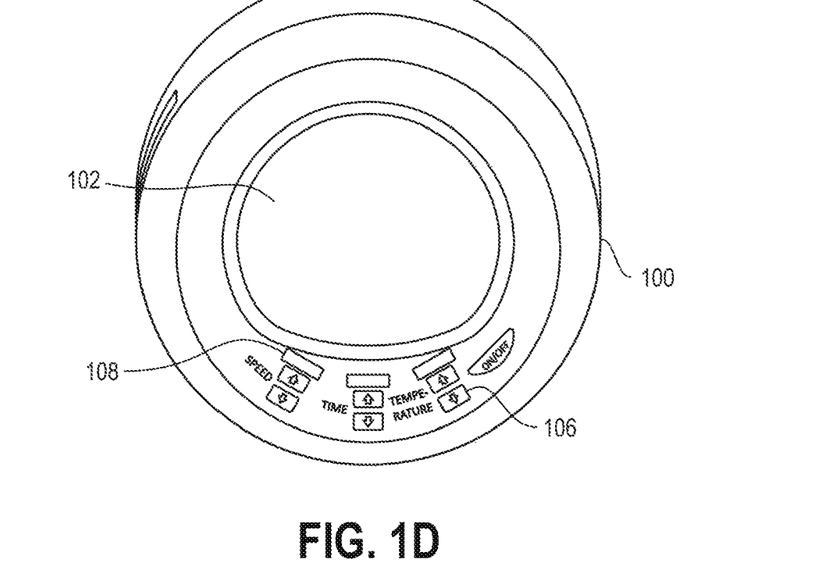
FIG. 1D illustrates a perspective view of the top housing of the automatic spin coating system shown in FIG. 1A.
Figure 1E:
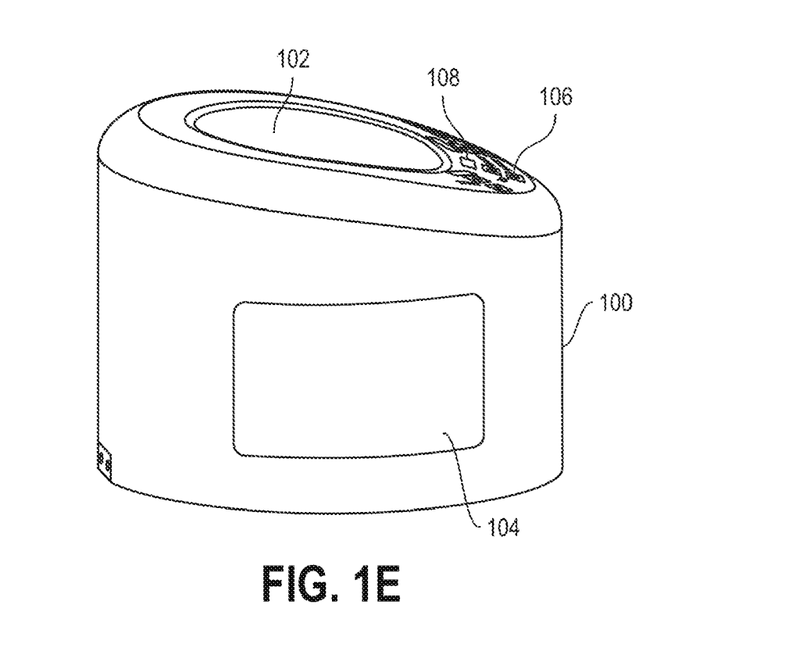
FIG. 1E illustrates a side perspective view of the top housing of the automatic spin coating system, where the top housing has transparent windows for inspection of a coating process.

FIGS. 1A and 1B illustrates an automatic spin coating system 10 comprising a top housing 100 and a bottom housing 110. The top housing 100 and a bottom housing 110 are enclosed together. Referring to FIGS. 1C and 1E, the top housing 100 has two transparent windows 102, 104 for inspection of the coating process. Window 102 is on top of the top housing, and window 104 is on side of the top housing. The top of the top housing 100, as shown in FIG. 1D, further has a LED display 108 and a control panel 106. In one embodiment, the control panel 108 has three parameters that allows users to manually control the coating process, including spin speed, substrate surface temperature and coating time.

Figure 2B:
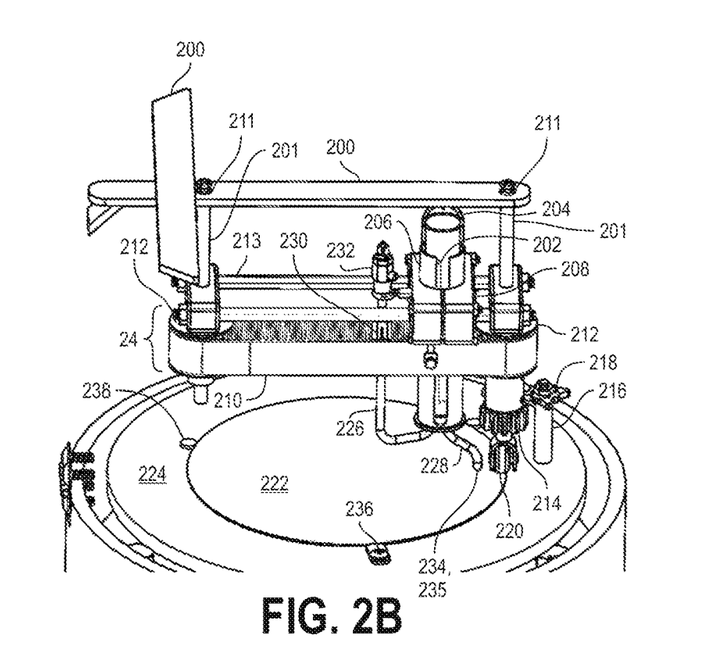
FIG. 2B illustrates a perspective view of the dispensing assembly and a portion of the bottom housing.
Figure 2C:
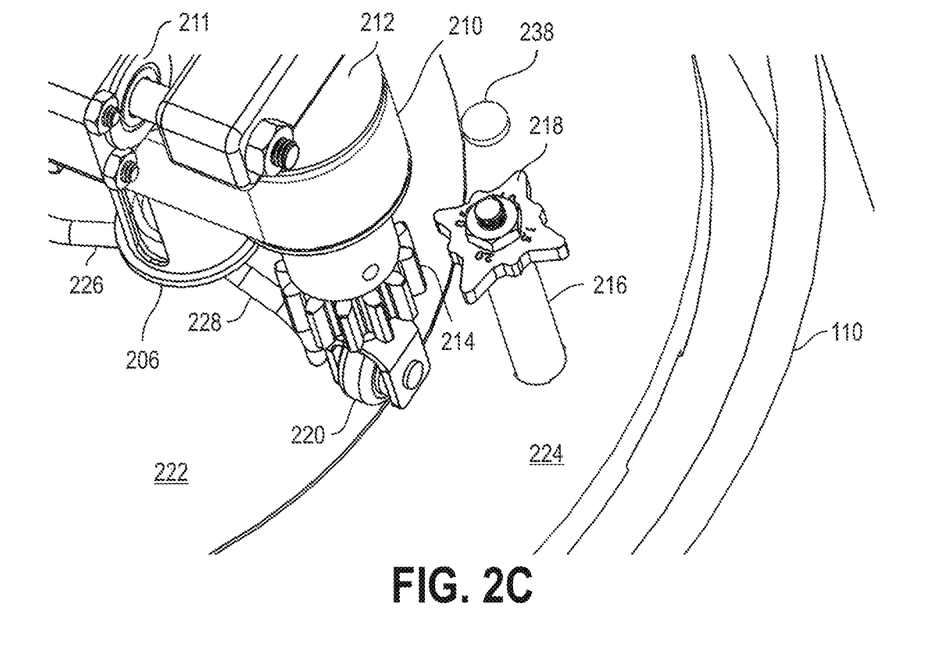
FIG. 2C illustrates a top perspective view of the drive gear, the smooth wheel, a portion of the pulley assembly and a stepper pin mounted on the chuck plate.
Figure 2D:
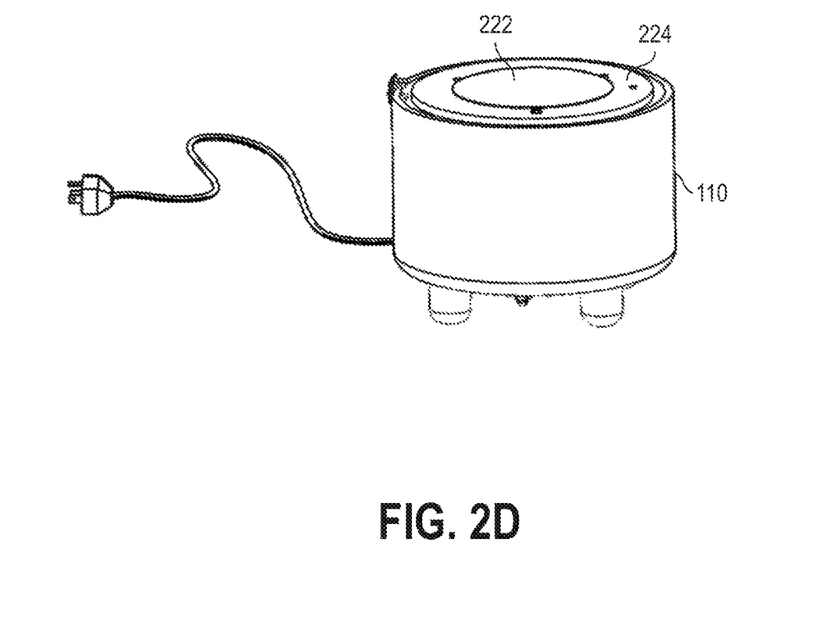
FIG. 2D illustrates a side view of the bottom housing of the spin coating system, where a base assembly is located inside the bottom housing.

Referring to FIGS. 2A and 2B, the automatic spin coating system 10 has the dispensing assembly 20 inside the top housing 100. The dispensing assembly 20 is comprised of a dispensing device 26, a pulley assembly 24, a drive gear 214 and a smooth wheel 220. The dispensing device 26 is connected to the pulley assembly 24, which in turn is connected to the drive gear 214 and a smooth wheel 220. In one embodiment, the dispensing device 26 has a vessel 204, held by a vessel holder 206 connected to an adaptor 208 that contains one or more sliding housings 211. The vessel 204 contains the coating material 202 to be dispensed from the dispensing device 26 from a first position to a second position. The vessel 204 can be a tube or a container. Also, referring to FIGS. 2A and 2B, the base assembly 22 is housed inside the bottom housing 110. The base assembly 22 is comprised of a coating plate 222 for receiving the coating material 202, a chuck plate 224 for securing the coating plate 222, and a stepper pin 216. The coating plate 222 can be a round substrate, for example, a glass disc. Referring to FIGS. 2C and 2F, the stepper pin 216 is mounted on the chuck plate 224 that is capable of engaging the drive gear 214 of the dispensing assembly 20. The drive gear 214 is touched and rotated by the stepper pin 216 that causes the linear movement of the dispensing device 26. At the same time, the coating plate 222 spins with the chuck plate 224 such that the coating material 202 is coated from a first circle to a second circle without overlap between circles on the coating plate 222 when the dispensing device 26 is moved from the first position to the second position by the pulley assembly 24.

In one embodiment, the pulley assembly 24 includes a pulley belt 210 and two pulley wheels 212 connected to the pulley belt 210. A pair of two rods 201 go through the two pulley wheels 212 and is mounted on the cross beam 200 at one end through the sliding housing 211. As shown in FIG. 2B, the vessel 204, the vessel holder 206 and the adaptor 208 are immobilized on the pulley belt 210 that move simultaneously with the pulley belt 210. The pulley belt 210 is driven by the two pulley wheels 212, which is rotated by the drive gear 214 that is touched and rotated by the stepper pin 216, as shown in FIG. 2C. The utilization of the pulley assembly 24 is to translate the angular rotation of the drive gear 214 to linear movement on rails 213 in radial direction.

Figure 2E:
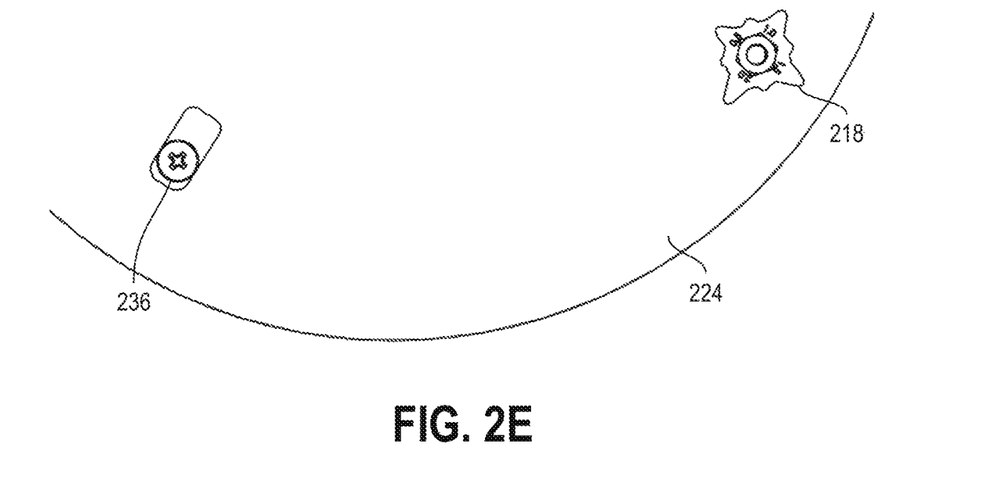
FIG. 2E illustrates a top view of a portion of the chuck plate, where the chuck plate has the stepper pin and a mobile pin.
Figure 2F:
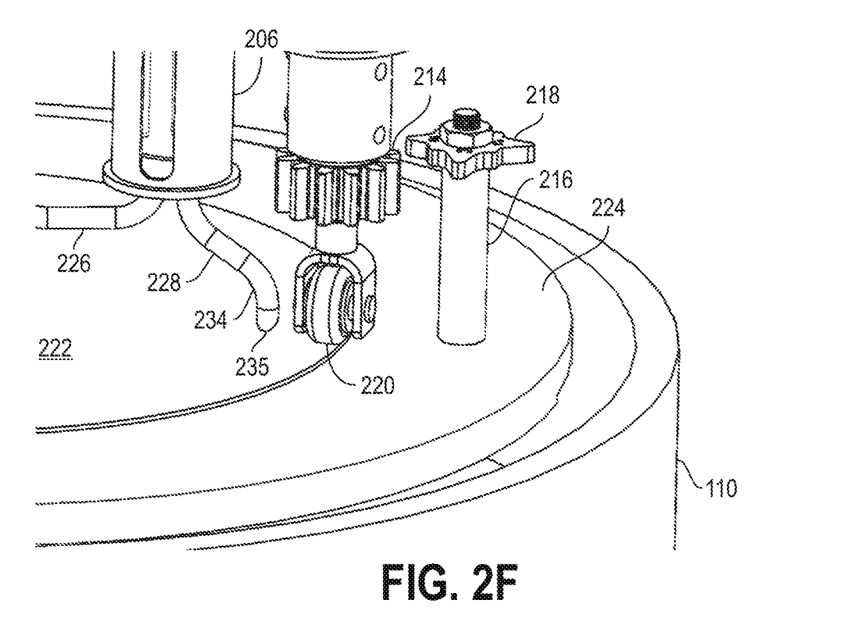
FIG. 2F illustrates a perspective view of a portion of the dispensing assembly and the bottom housing, where the smooth wheel touches along the edge of the coating plate.

In one embodiment, the stepper pin 216 has a gear 218 with teeth at different sizes, including 0.5, 1.0, 1.5 and 2.0 mm, as shown in FIGS. 2C and 2E. Differently sized teeth of the gear 218 allow different degrees of the movements of the dispensing device 26 on rails 213. The gear 218 of the stepper pin 216 can be adjusted manually. More sophisticated stepper pin 216 could be incorporated for continuously variable electronic control of gears or replaced by an electromechanical optical rotary encoder to trigger linear stepper movement.

In one embodiment, as shown in FIG. 2F, the dispensing assembly 20 includes a smooth wheel 220 that spins with the spinning coating plate 222 while keeping the dispensing assembly 20 in the stationary position. The function of the smooth wheel 220 is to support the weight of the dispensing assembly 20 and to maintain constant space between the coating plate 222 and the dispensing assembly 20. The smooth wheel 220 is capable of detecting the surface flatness variation of the coating plate 222 by touching the edge of the coating plate 222, so that the dispensing assembly 20 can adjust the height relative to the base assembly 22 through the sliding housing 211 inside the cross beam 200 to maintain constant space between the coating plate 222 and the dispensing assembly 20, especially the dispense nozzle 234 when the surface flatness of substrate is variable.

Figure 2G:
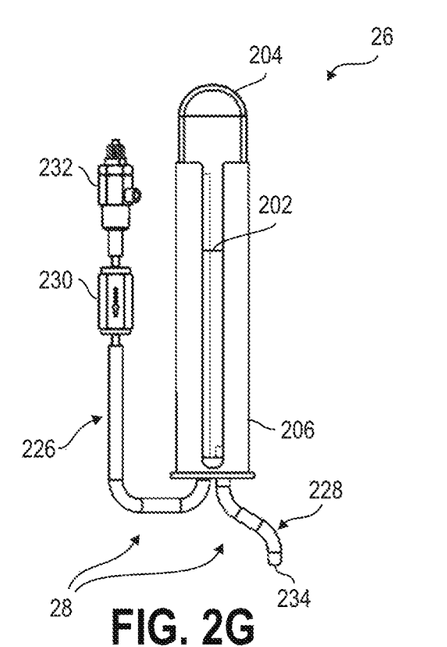
FIG. 2G illustrates a side view of the dispensing device of the dispensing assembly shown in FIG. 2A, including a vessel assembly and a tubing assembly.
Figure 2H:
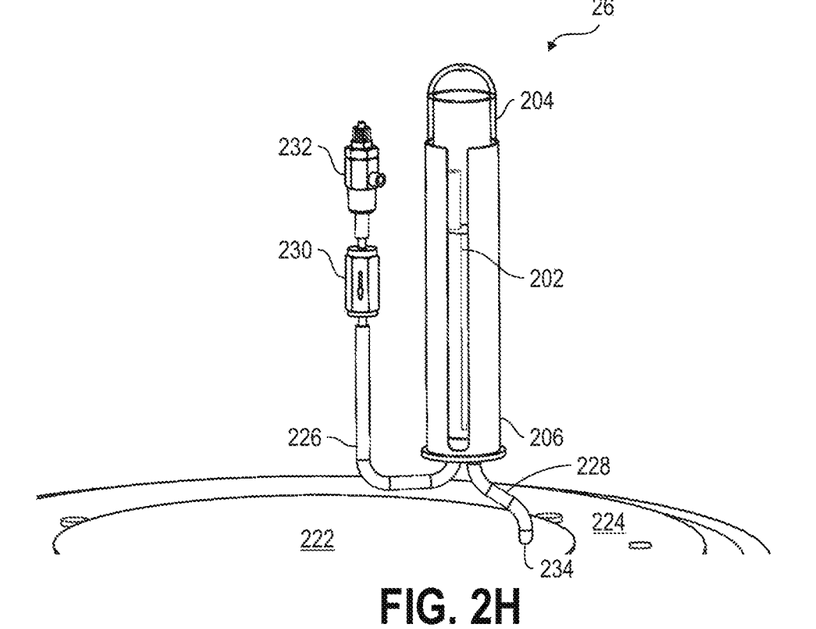
FIG. 2H illustrates a perspective view of the dispensing device of the dispensing assembly, where the tubing assembly is mounted on a vessel holder and controls the flow of coating material toward the coating plate.
Figure 2I:
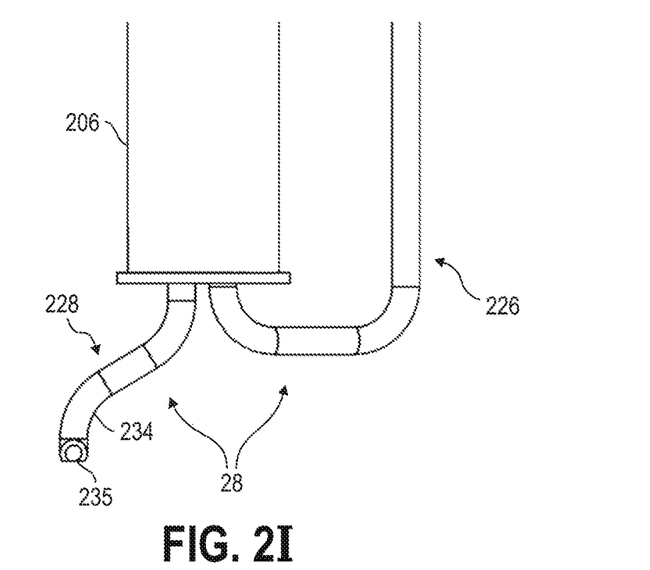
FIG. 2I illustrates a side view of the tubing assembly shown in FIG. 2H, having a first tubing and a second tubing mounted on the vessel holder and inserted into the vessel.
Figure 2J:
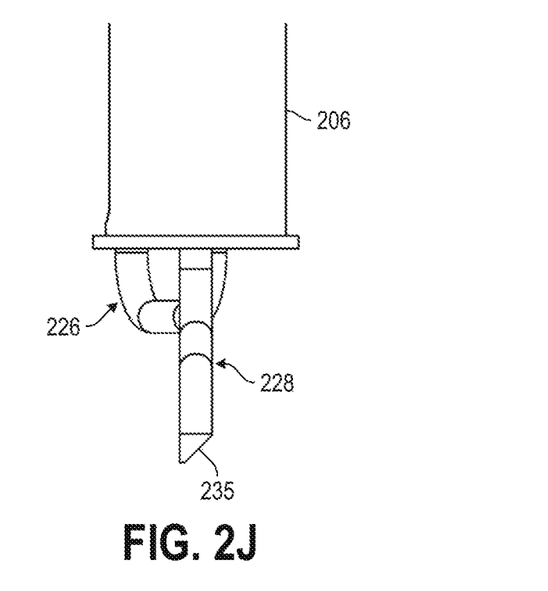
FIG. 2J illustrates a side view of a portion of the dispensing device shown in FIG. 2H, where the second tubing has a bevel-tip nozzle.

In one embodiment, as shown in FIG. 2G, the dispensing device 26 further has a tubing assembly 28, including a first tubing 226 and a second tubing 228. The tubing assembly 28 is mounted to the vessel holder 206 and inserted to the vessel 204. As shown in FIGS. 2G and 2H, the first tubing 226 includes a check valve 230 and an air venting valve 232. The check valve 230 provides one-direction flow in the first tubing 226. The air venting valve 232 releases vacuum inside the vessel 204 and accurately controls the flow of the coating material 202. The second tubing 228 has a dispense nozzle 234 with bevel tip 235 for automatic delivery of the coating material 202 to the coating plate 222 as shown in FIGS. 2I and 2J. The bevel-tip nozzle 234, 235, as shown in FIG. 2J, supplies the coating material 202 only when the coating material 202 is consumed on the coating plate 222. The nozzle 234 reliably provides even flow to prevent overflow, inconsistent flow, and other irregular flow patterns. The bevel tip 235 is shaped similar to the spreader slide which spreads the coating material 202 with a constant angle on the microscope slide. The bevel tip 235 of the nozzle 234 is not necessarily in contact with the coating plate 222. The contact angle of 10~45° for the bevel tip 235 has been tested optimally for spin coating. If the contact angle is greater, the coated film would be thicker, provided that the nozzle size is fixed and other dispense factors are constant.

To allow the coating material 202 to be dispensed from the first position to the second position, the dispensing device 26 moves by the rotating pulley assembly 24 connected to the drive gear 214, in which the drive gear 214 is touched by the stepper pin 216 that revolves when the chuck plate 224 spins. Due to the spinning of the chuck plate 224, the coating material 202 is coated in monolayered circles on the coating plate 222 from the first circle to the second circle when the coating material 202 is dispensed from the dispensing device 26 from the first position to the second position.

Figure 1F:
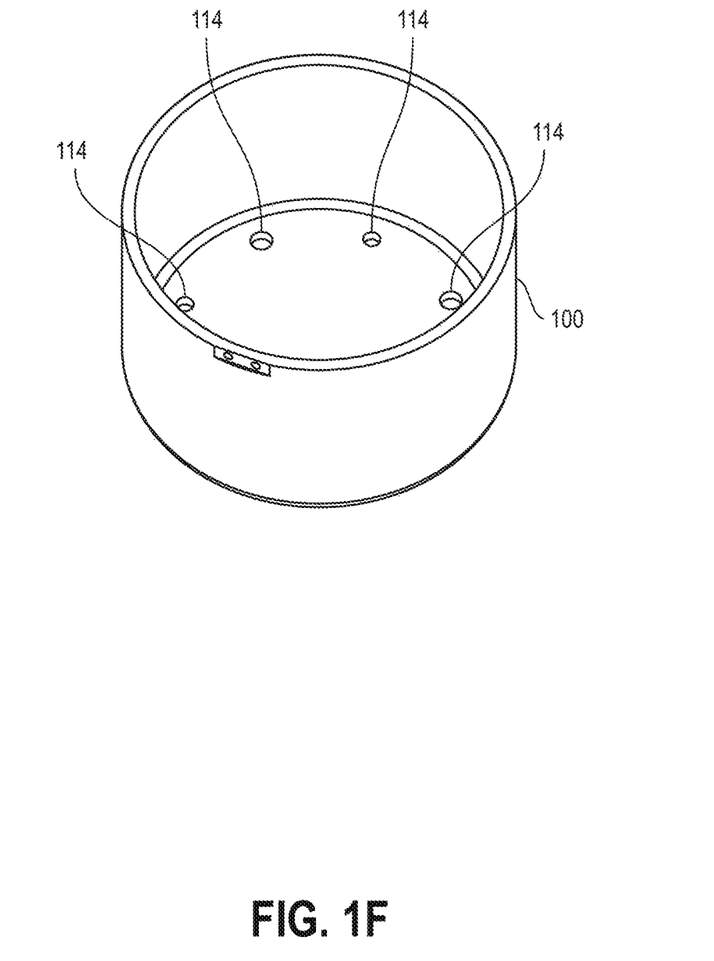
FIG. 1F illustrates a perspective view of the inside of the bottom housing, having holes fastened with rubber cushion feet and spacers of a base assembly.
Figure 3A:
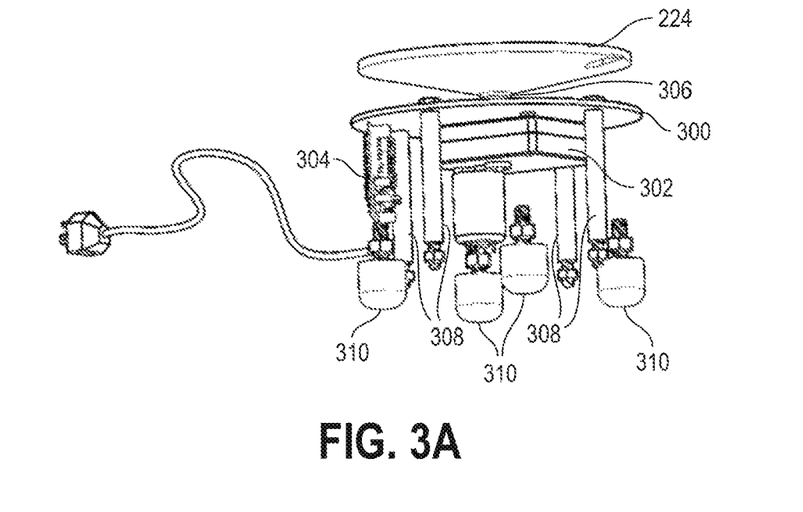
FIG. 3A illustrates a perspective view of the base assembly.
Figure 3B:
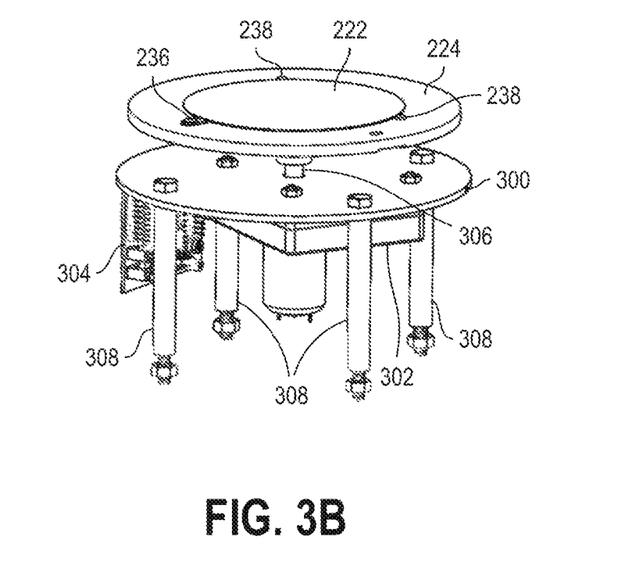
FIG. 3B illustrates a perspective view of the base assembly having the coating plate, the chuck plate, a mounting plate under the chuck plate, where the mounting plate is attached with a motor and a control board.
Figure 3C:
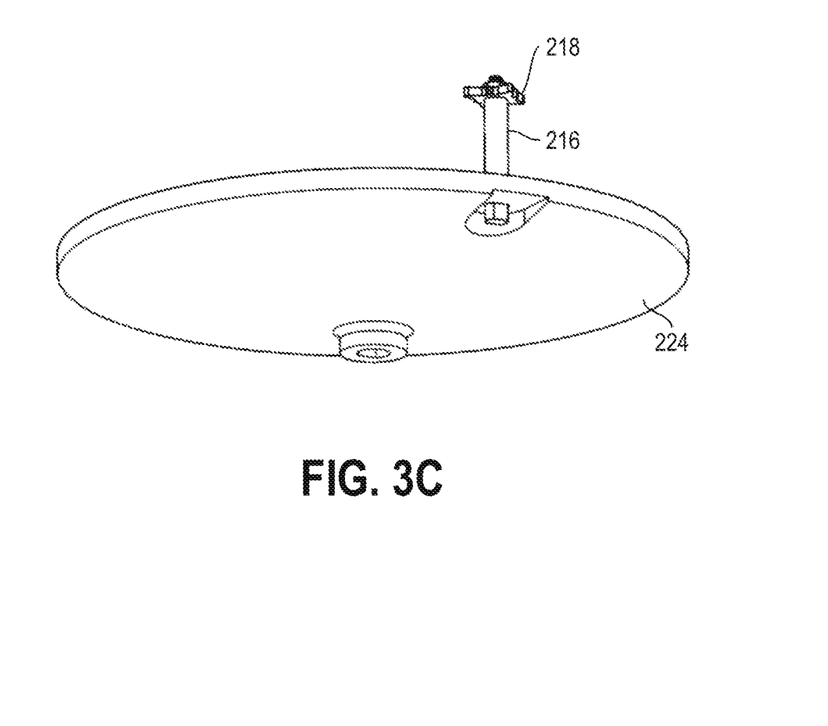
FIG. 3C illustrates a bottom perspective view of the chuck plate of the base assembly.

In one embodiments, FIGS. 3A and 3B illustrates the structure of the base assembly 22 inside the bottom housing 110, including a control board 304, an electric motor 302, a mounted plate 300, spacers 308, and rubber cushion feet 310. The motor 302 and the control board 304 are immobilized on the mounted plate 300. The mounted plate 300 is fixed to the bottom of the bottom housing 110 by the spacers 308. The rubber cushion feet 310 are fastened to the bottom holes 114 of the bottom housing 110, as shown in FIG. 1F. As shown in FIG. 3E, the chuck plate 224 is connected to the motor through a shaft 306. The control board 304 is a printed circuit board with electronic components for controlling all elements in the automatic spin coating system 10, including motor control and temperature control.

Figure 3D:
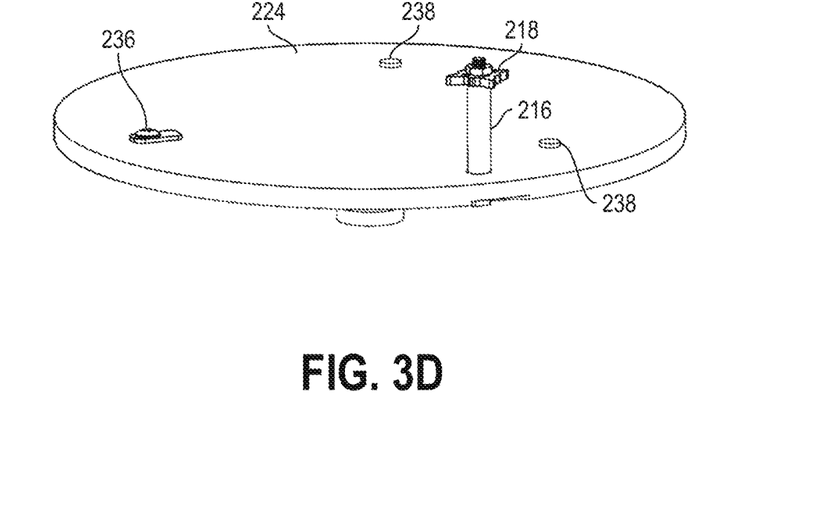
FIG. 3D illustrates a perspective view of the chuck plate of the base assembly showing the stepper pin, the mobile pin and two immobile pins.
Figure 3E:
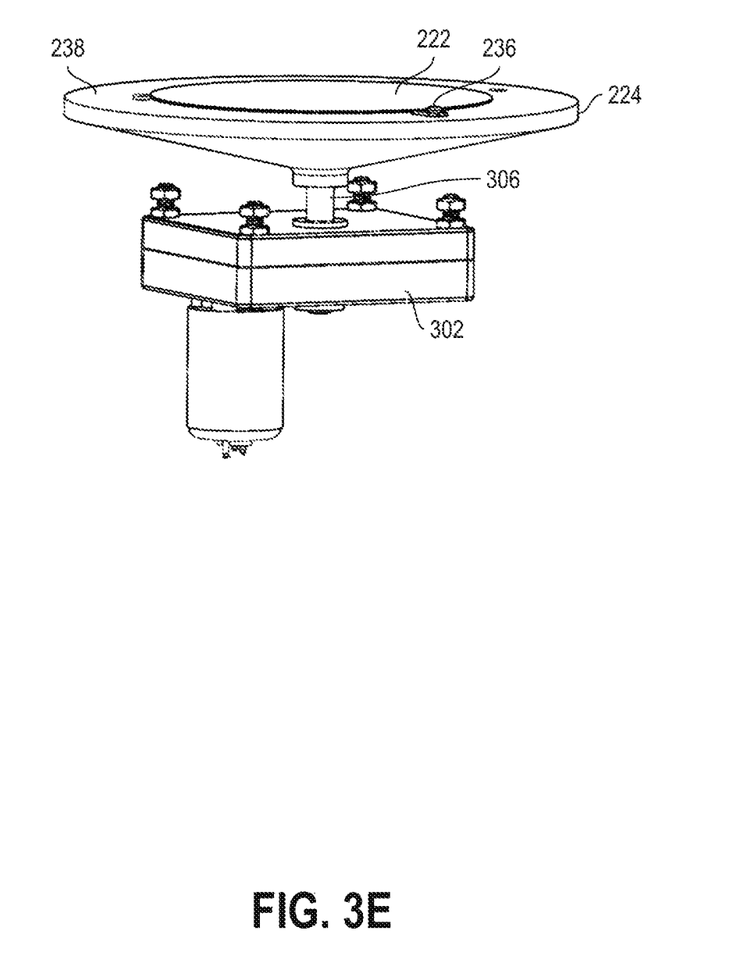
FIG. 3E illustrates a perspective view of a portion of the base assembly where the chuck plate is mounted to the shaft of the motor.

In one embodiment, the chuck plate 224 is utilized to hold the coating plate 222 in place by two immobile pins 238 and one mobile pin 236, as shown in FIG. 3D. The coating plate 222 can be a glass disc or any round substrate, and is for receiving the coating material 202. The cooling and heating elements are enclosed in the chuck plate 224. The stepper pin 216 is mounted on the chuck plate 224 at predetermined radius.

III. Operation

In one embodiment, the method of the automatic spin coating system 10 comprises rotating the chuck plate 224 continuously by the motor 302, and moving the dispensing device 26 once every complete revolution from the first position to the second position by the pulley assembly 24. The coating material 202 loaded in the vessel 204 is discharged from the dispensing device 26 toward the rotating coating plate 222 secured on the chuck plate 224. The coating parameters are controlled by the control panel 106 on the top housing 100. In one embodiment, the temperature of coating plate 222 can be accurately controlled to preserve viability and morphology of the coating materials 202.

In one embodiment, the moving step of the automatic spin coating system 10 is accomplished by rotating the drive gear 214 connected to the pulley assembly 24. The drive gear 214 is rotated by the stepper pin 216 so as to cause the movement of the dispensing device 26. The dispensing device 26 has one or more sliding housings 211 inside the adaptor 208, which stabilize and smooth the movement of the dispensing device 26 on rails 213.

In one preferred embodiment, the smooth wheel 220 is rolling and remains stationary on the spinning chuck plate 224. The stepper pin 216 is rotated by the chuck plate 224 that engages the drive gear 214 of the dispensing assembly 20. The stepper pin 216, the drive gear 214 and the pulley assembly 24 translate the angular rotation of the coating place 222 to the linear movement of the dispensing device 26 on rails 213 in the radial direction. The stationary rolling step of the smooth wheel 220 is to maintain the constant space between the coating plate 222 and the dispensing device 26.

IV. Experiments

Example Result 1

Figure 4:
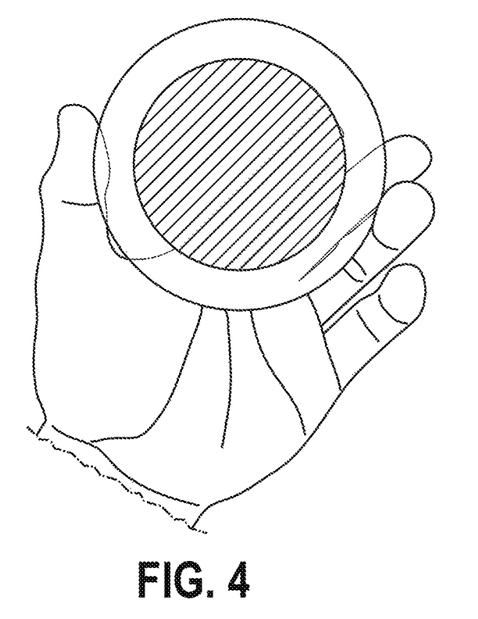
FIG. 4 illustrates an example of a thin monolayer blood coating on the coating plate.

As an example 1, an experiment of the automatic spin coating system 10 is carried out for making a thin monolayer blood coating. As shown in FIG. 4, fresh peripheral whole blood was spin-coated on a 100 mm-diameter glass disc at spin speed of 60 RPM, bevel-tip contact angle of 10°, tip-substrate space of 0.1 mm, nozzle size of 23 gauge, stepper pin's scale of 0.5 mm, and substrate temperature of 22° C. The blood was directly dispensed from a 4 mL BD Vacutainer K2-EDTA lavender tube with conventional closure. The resulted monolayer blood film had a single layer of dispersed blood cells with intact morphology across the entire glass disc.

Example Result 2

Figure 5:
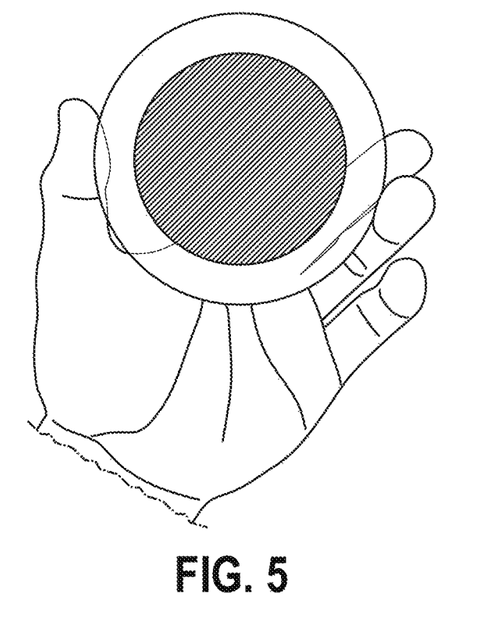
FIG. 5 illustrates an example of a thick monolayer blood coating on the coating plate.

As an example 2, an experiment of the automatic spin coating system 10 is carried out for making a thick monolayer blood coating. As shown in FIG. 5, approximately 1 mL of peripheral whole blood from a cancer patient has been spin-coated and fully dried on a 100 mm-diameter glass disc at spin speed of 30 RPM, bevel-tip contact angle of 45°, tip-substrate space of 0.3 mm, nozzle size of 23 gauge, stepper pin's scale of 1 mm, and substrate temperature of 37° C. The blood was directly dispensed from a 10 mL CellSave preservative evacuated tube. The thick blood film, as shown in FIG. 5, has been used for identification, enumeration, and examination of rare tumor cells in the peripheral blood.

The above descriptions are those of current embodiments of the invention. Various alterations and changes can be made without departing from the spirit and broader aspects of the invention, which are to be interpreted in accordance with the principles of patent law including the Doctrine of Equivalents.

What is claimed is:

1. A spin coating apparatus, comprising:
a dispensing assembly; and
a base assembly;
said dispensing assembly further comprising:
i) a dispensing device;
ii) a pulley assembly connected to said dispensing device;
iii) a drive gear connected to said pulley assembly;
iv) a smooth wheel connected to said drive gear;
said base assembly further comprising:
i) a coating plate, said coating plate touched with said smooth wheel;
ii) a chuck plate capable of spinning;
iii) a stepper pin mounted on said chuck plate;
wherein when said drive gear is touched by said stepper pin, said dispensing device moves by said pulley assembly that is rotated by said drive gear; and
said spin coating apparatus further comprising an airtight enclosure that is separated into a bottom housing and a top housing, said bottom housing connected to said base assembly and said top housing connected to said dispensing assembly.

2. The spin coating apparatus of claim 1, wherein said pulley assembly further comprising:
a pulley belt;
a pair of pulley wheels connected to said pulley belt;
one of said pair of pulley wheels connected to said drive gear;
wherein when said drive gear is touched and rotated by said stepper pin, said pulley wheels move said pulley belt to move said dispensing device from a first position to a second position.

3. The spin coating apparatus of claim 2, wherein said pulley assembly includes one or more rails, wherein said dispensing device moves from said first position to said second position through said rails.

4. The spin coating apparatus of claim 2, wherein said pulley assembly includes one or more sliding housings inside the cross beam, wherein the movement of said dispensing assembly is stabilized and smoothed by said sliding housings.

5. A spin coating apparatus, comprising:
a dispensing assembly for dispensing a coating material; and
a base assembly;
said dispensing assembly further comprising:
i) a dispensing device, said dispensing device having a vessel assembly that contains said coating material to be dispensed from a first position to a second position;
ii) a pulley assembly connected to said dispensing device;
iii) said pulley assembly further comprising: a pulley belt a pair of pulley wheels connected to said pulley belt one of said pair of pulley wheels connected to said drive gear;
wherein when said drive gear is touched and rotated by said stepper pin, said pulley wheels move said pulley belt to move said dispensing device from said first position to said second position;
iv) a drive gear connected to said pulley assembly; and
v) a smooth wheel connected to said drive gear;
said based assembly further comprising:
i) an electric motor;
ii) a coating plate for receiving said coating material, said coating plate touched with said smooth wheel;
iii) a chuck plate for securing said coating plate, said chuck plate capable of spinning by said electric motor;
iv) a stepper pin mounted on said chuck plate, said stepper pin capable of engaging said drive gear of said dispensing assembly; and
wherein when said chuck plate spins, said stepper pin revolves and touches said drive gear, thereby causing said drive gear to rotate said pulley assembly;
wherein when said drive gear is touched by said stepper pin, said dispensing device moves from said first position to said second position by said rotating pulley assembly such that said coating material is coated in circles on said coating plate;
wherein said smooth wheel is capable of detecting the surface flatness variation of said coating plate by touching the edge of said coating plate to maintain constant space between said coating plate and said dispensing assembly.

* * * * *